(12) United States Patent
Somekh et al.

(10) Patent No.: US 11,376,003 B2
(45) Date of Patent: Jul. 5, 2022

(54) SURGICAL HANDLE ARTICULATION ASSEMBLY

(71) Applicant: Lexington Medical, Inc., Billerica, MA (US)

(72) Inventors: Gonen Somekh, Kerem Maharal (IL); Leon Amariglio, Lexington, MA (US)

(73) Assignee: Lexington Medical, inc., Bedford, MA (US)

( * ) Notice: Subject to any disclaimer, the term of this patent is extended or adjusted under 35 U.S.C. 154(b) by 155 days.

(21) Appl. No.: 16/027,579

(22) Filed: Jul. 5, 2018

(65) Prior Publication Data
US 2020/0008801 A1    Jan. 9, 2020

(51) Int. Cl.
*A61B 17/072* (2006.01)
*A61B 17/29* (2006.01)
*A61B 17/00* (2006.01)

(52) U.S. Cl.
CPC .... *A61B 17/07207* (2013.01); *A61B 17/2909* (2013.01); *A61B 2017/0023* (2013.01); *A61B 2017/00473* (2013.01); *A61B 2017/00862* (2013.01); *A61B 2017/07271* (2013.01); *A61B 2017/2901* (2013.01); *A61B 2017/2925* (2013.01)

(58) Field of Classification Search
USPC ...................................................... 227/177.1
See application file for complete search history.

(56) References Cited

U.S. PATENT DOCUMENTS

| RE28,932 | E | 8/1976 | Noiles et al. |
| 4,737,608 | A * | 4/1988 | Jones ............... H01H 21/50 200/300 |
| 4,978,049 | A | 12/1990 | Green |
| 5,300,081 | A | 4/1994 | Young et al. |
| 5,326,013 | A | 7/1994 | Green et al. |
| RE34,680 | E | 8/1994 | Lieser |
| 5,489,292 | A | 2/1996 | Tovey et al. |
| 5,507,426 | A | 4/1996 | Young et al. |

(Continued)

FOREIGN PATENT DOCUMENTS

| EP | 1021130 | 11/2006 |
| EP | 2886020 | 6/2015 |

(Continued)

OTHER PUBLICATIONS

International Searching Authority., International Search Report and Written Opinion dated Oct. 4, 2019 for PCT Application No. PCT/US2019/040315 Filed Jul. 2, 2019, 9 pages.

(Continued)

*Primary Examiner* — Chinyere J Rushing-Tucker
(74) *Attorney, Agent, or Firm* — Brooks, Cameron & Huebsch, PLLC (57) ABSTRACT

The present disclosure includes apparatuses for a surgical handle assembly. An example apparatus includes a reloadable cartridge assembly and a surgical handle assembly including an articulation assembly configured to maintain the reloadable cartridge assembly in a first operation position, the articulation assembly comprising a knob in a first knob position coupled to a housing and a spring coupled to the housing configured to bias a sphere radially outward to a first slot of a radial position component.

20 Claims, 7 Drawing Sheets

(56) References Cited

U.S. PATENT DOCUMENTS

| | | | |
|---|---|---|---|
| 5,601,224 A * | 2/1997 | Bishop | A61B 17/0682 227/175.1 |
| 5,762,256 A | 6/1998 | Mastri et al. | |
| 5,823,066 A * | 10/1998 | Huitema | A61B 17/07207 74/527 |
| 5,865,361 A | 2/1999 | Milliman et al. | |
| 5,901,895 A | 5/1999 | Heaton et al. | |
| 6,109,500 A | 8/2000 | Alli et al. | |
| 6,281,453 B1 * | 8/2001 | Uleski | B60Q 1/0076 200/4 |
| 6,302,798 B1 * | 10/2001 | Nakaguro | F16D 7/06 192/56.33 |
| 7,044,353 B2 | 5/2006 | Mastri et al. | |
| 7,380,696 B2 | 6/2008 | Shelton, IV et al. | |
| 7,404,508 B2 | 7/2008 | Smith et al. | |
| 7,455,208 B2 | 11/2008 | Wales et al. | |
| 7,624,902 B2 | 12/2009 | Marczyk et al. | |
| 7,837,079 B2 | 11/2010 | Holsten et al. | |
| 7,845,535 B2 | 12/2010 | Scircia | |
| 8,020,743 B2 | 9/2011 | Shelton, IV | |
| 8,061,576 B2 | 11/2011 | Cappola | |
| 8,235,274 B2 | 8/2012 | Cappola | |
| 8,328,822 B2 | 12/2012 | Huitema et al. | |
| 8,336,754 B2 | 12/2012 | Cappola et al. | |
| 8,413,868 B2 | 4/2013 | Cappola | |
| 8,573,460 B2 | 11/2013 | Cappola | |
| 8,573,463 B2 * | 11/2013 | Scirica | A61B 17/07207 227/179.1 |
| 8,608,043 B2 | 12/2013 | Scirica | |
| 8,622,894 B2 | 1/2014 | Banik et al. | |
| 8,695,865 B2 | 4/2014 | Smith et al. | |
| 8,888,814 B2 | 11/2014 | Cappola | |
| 9,204,876 B2 | 12/2015 | Cappola et al. | |
| 9,655,617 B2 | 5/2017 | Cappola | |
| 9,931,739 B2 * | 4/2018 | Nelson | B25B 15/04 |
| 2001/0030219 A1 | 10/2001 | Green et al. | |
| 2004/0232199 A1 | 11/2004 | Shelton, IV et al. | |
| 2005/0006429 A1 * | 1/2005 | Wales | A61B 17/07207 227/175.1 |
| 2006/0111210 A1 | 5/2006 | Hinman | |
| 2007/0262116 A1 | 11/2007 | Hueil et al. | |
| 2008/0083810 A1 | 4/2008 | Marczyk | |
| 2008/0179374 A1 | 7/2008 | Beardsley et al. | |
| 2009/0062614 A1 | 3/2009 | Adzich et al. | |
| 2009/0272614 A1 * | 11/2009 | Watarai | F16D 3/12 192/70.17 |
| 2010/0264193 A1 | 10/2010 | Huang et al. | |
| 2011/0062211 A1 * | 3/2011 | Ross | A61B 17/07207 227/175.1 |
| 2013/0092719 A1 * | 4/2013 | Kostrzewski | A61B 17/068 227/177.1 |
| 2013/0098966 A1 | 4/2013 | Kostrzewski et al. | |
| 2013/0199327 A1 | 8/2013 | Park et al. | |
| 2013/0245676 A1 * | 9/2013 | Cappola | A61B 17/07207 606/213 |
| 2014/0276949 A1 | 9/2014 | Staunton et al. | |
| 2015/0196996 A1 * | 7/2015 | Nelson | B25G 1/085 81/63.1 |
| 2015/0342605 A1 | 12/2015 | Abbott et al. | |
| 2016/0166250 A1 * | 6/2016 | Marczyk | A61B 17/068 227/176.1 |
| 2017/0000485 A1 | 1/2017 | Shelton, IV et al. | |
| 2017/0172577 A1 | 6/2017 | Wenchell et al. | |
| 2017/0281177 A1 | 10/2017 | Harris et al. | |
| 2017/0281220 A1 * | 10/2017 | Hibner | A61B 17/320092 |
| 2018/0078354 A1 | 3/2018 | Cardinale et al. | |
| 2018/0289370 A1 | 10/2018 | Amariglio et al. | |
| 2018/0368832 A1 | 12/2018 | Marecki et al. | |
| 2020/0008801 A1 | 1/2020 | Somekh et al. | |

FOREIGN PATENT DOCUMENTS

| | | |
|---|---|---|
| EP | 2484290 | 7/2015 |
| EP | 2311385 | 5/2017 |

OTHER PUBLICATIONS

International Searching Authority., International Search Report and Written Opinion dated Jun. 18, 2018 tor PCT Application No. PCT/US2018/025988 Filed Apr. 4, 2018, 9 pages.

International Searching Authority., International Search Report and Written Opinion dated Oct. 22, 2018 for PCT Application No. PCT/US2018/038909, Filed Jun. 22, 2018, 10 pages.

\* cited by examiner

SURGICAL HANDLE ARTICULATION ASSEMBLY

TECHNICAL FIELD

The present disclosure relates generally to a surgical handle assembly, and more particularly, to an articulation assembly of a surgical handle assembly.

BACKGROUND

A surgical handle assembly can be used in a number of surgical devices. One example includes use as a surgical stapler. A surgical stapler is a fastening device used to clamp tissue between opposing jaw structures to join tissue using surgical fasteners. Surgical staplers can include two elongated members used to clamp the tissue. One of the elongated members can include one or more reloadable cartridges and the other elongated member can include an anvil that can be used to form a staple when driven from the reloadable cartridge. A surgical stapler can receive one or more reloadable cartridges. An example of reloadable cartridges can include having rows of staples having a linear length. For example, a row of staples can have a linear length between 30 mm and 60 mm. A staple can be ejected by actuation of a movable handle member that is a part of the surgical handle assembly of the surgical stapler.

DETAILED DESCRIPTION

The present disclosure includes apparatuses for a surgical handle assembly. An example apparatus includes a reloadable cartridge assembly and a surgical handle assembly including an articulation assembly configured to maintain the reloadable cartridge assembly in a first operation position. In some examples, the articulation assembly can include a knob in a first knob position coupled to a housing and a spring coupled to the housing configured to bias a sphere radially outward to a first slot of a radial position component.

In a number of embodiments, the articulation assembly is configured to maintain the reloadable cartridge assembly in one of a plurality of operation positions. For example, the articulation assembly can be configured to maintain the reloadable cartridge assembly in the first operation position.

In a number of embodiments, the reloadable cartridge assembly can be configured to rotate about an axis of a particular plane from the first operation position to a second operation position. The articulation assembly can be configured to actuate the reloadable cartridge assembly from the first operation position to the second operation position. In some examples, the first operation position of the reloadable cartridge assembly can be approximately 90 degrees from another operation position.

The articulation assembly can include a knob, a cam, a housing, one or more springs, one or more spheres, a tab, an articulation arm, a radial position component, and a bottom. The knob can be coupled to the housing via the cam. The housing and the cam can actuate rotationally in response to the knob being rotationally actuated by a user.

The housing can include one or more openings. The one or more springs and the one or more spheres can be in the one or more openings of the housing. The one or more springs can bias the one or more spheres radially outward from the housing to contact one or more slots in the radial position component. The one or more spheres contacting the one or more slots in the radial position component can maintain the articulation assembly in that knob position until the knob is actuated rotationally by the user. Each slot in the radial position component can correspond to a knob position.

In a number of embodiments, the cam can be coupled to a tab and the tab can be coupled to an articulation arm. The tab and the articulation arm can move in a linear direction in response to the cam and the knob being actuated rotationally.

The articulation arm can be coupled to the reloadable cartridge assembly. The reloadable cartridge assembly can rotate from a first operation position to a second operation position in response to the articulation arm moving in a linear direction, as a result of the user rotating the knob.

In the following detailed description of the present disclosure, reference is made to the accompanying drawings that form a part hereof, and in which is shown by way of illustration how one or more embodiments of the disclosure may be practiced. These embodiments are described in sufficient detail to enable those of ordinary skill in the art to practice the embodiments of this disclosure, and it is to be understood that other embodiments may be utilized and that process, electrical, and structural changes may be made without departing from the scope of the present disclosure.

As used herein, designators such as "X", "Y", "N", "M", etc., particularly with respect to reference numerals in the drawings, indicate that a number of the particular feature so designated can be included. It is also to be understood that the terminology used herein is for the purpose of describing particular embodiments only and is not intended to be limiting. As used herein, the singular forms "a", "an", and "the" can include both singular and plural referents, unless the context clearly dictates otherwise. In addition, "a number of", "at least one", and "one or more" (e.g., a number of pivot points) can refer to one or more pivot points, whereas a "plurality of" is intended to refer to more than one of such things. Furthermore, the words "can" and "may" are used throughout this application in a permissive sense (i.e., having the potential to, being able to), not in a mandatory sense (i.e., must). The term "include," and derivations thereof, means "including, but not limited to". The terms "coupled" and "coupling" mean to be directly or indirectly connected physically or for access to and movement of the movable handle member, as appropriate to the context.

The figures herein follow a numbering convention in which the first digit or digits correspond to the figure number and the remaining digits identify an element or component in the figure. Similar elements or components between different figures may be identified by the use of similar digits. For example, 222 may reference element "22" in FIG. 2, and a similar element may be referenced as 322 in FIG. 3A. As will be appreciated, elements shown in the various embodiments herein can be added, exchanged, and/or eliminated so as to provide a number of additional embodiments of the present disclosure. In addition, the proportion and/or the relative scale of the elements provided in the figures are intended to illustrate certain embodiments of the present disclosure and should not be taken in a limiting sense.

Figure 1:
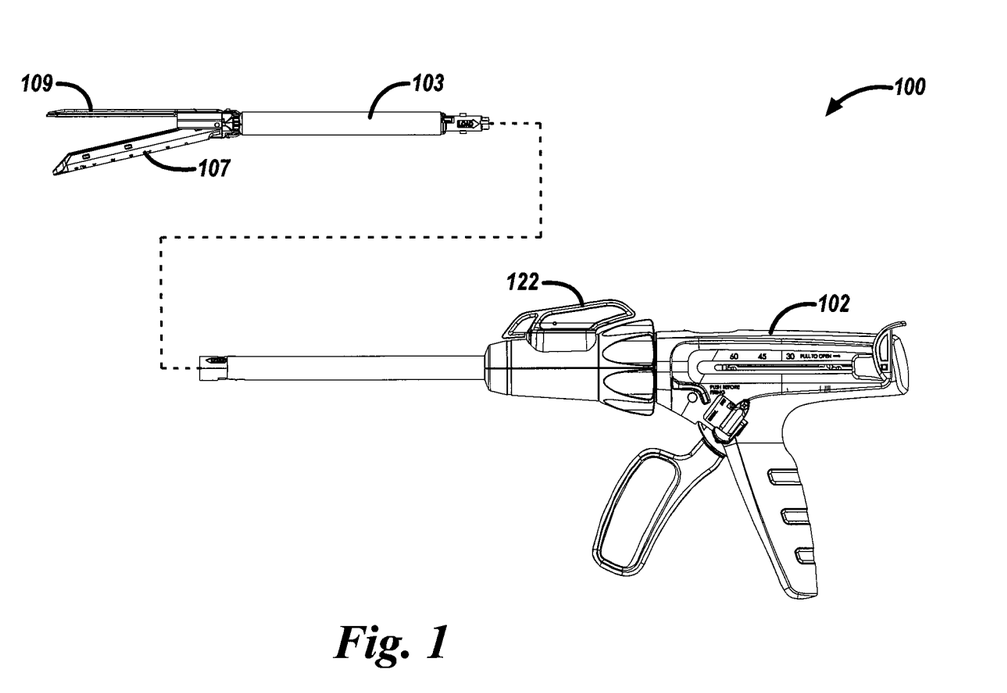
FIG. 1 is a schematic diagram of an apparatus including a surgical handle assembly and a reloadable cartridge assembly in accordance with a number of embodiments of the present disclosure.

FIG. 1 is a schematic diagram of an apparatus 100 including a surgical handle assembly 102 and a reloadable cartridge assembly 103 in accordance with a number of embodiments of the present disclosure. In the example, the apparatus 100 can be a surgical stapler, for example.

As shown in the example of FIG. 1, the reloadable cartridge assembly 103, e.g. a disposable loading unit, can be releasably secured to a distal end of an elongated body of the surgical handle assembly 102. In this example, the reloadable cartridge assembly 103 can include a first elongated member 107 and a second elongated member 109 that can be used to clamp tissue. One of the elongated members can house one or more staple cartridges. The other elongated member can have an anvil that can be used to form a staple when driven from the staple cartridge. As mentioned, an apparatus 100 can receive reloadable cartridge assemblies having rows of staples. In a number of embodiments, third party reloadable cartridge and/or reloadable cartridge assemblies may be used with the surgical handle assembly 102 and embodiments of surgical handle assembly 102 may be configured to receive the same.

The reloadable cartridge assembly 103 can be actuated using a knob 122 to reach a stapling site and position the reloadable cartridge assembly 103 at a particular angle for stapling. The knob 122 can be configured to actuate rotationally and the reloadable cartridge assembly 103 can rotate about an axis of a particular plane in response to the knob 122 being actuated rotationally by a user. In some examples, the position of the reloadable cartridge assembly 103 can be maintained in response to the knob 122 maintaining its position.

Figure 2:
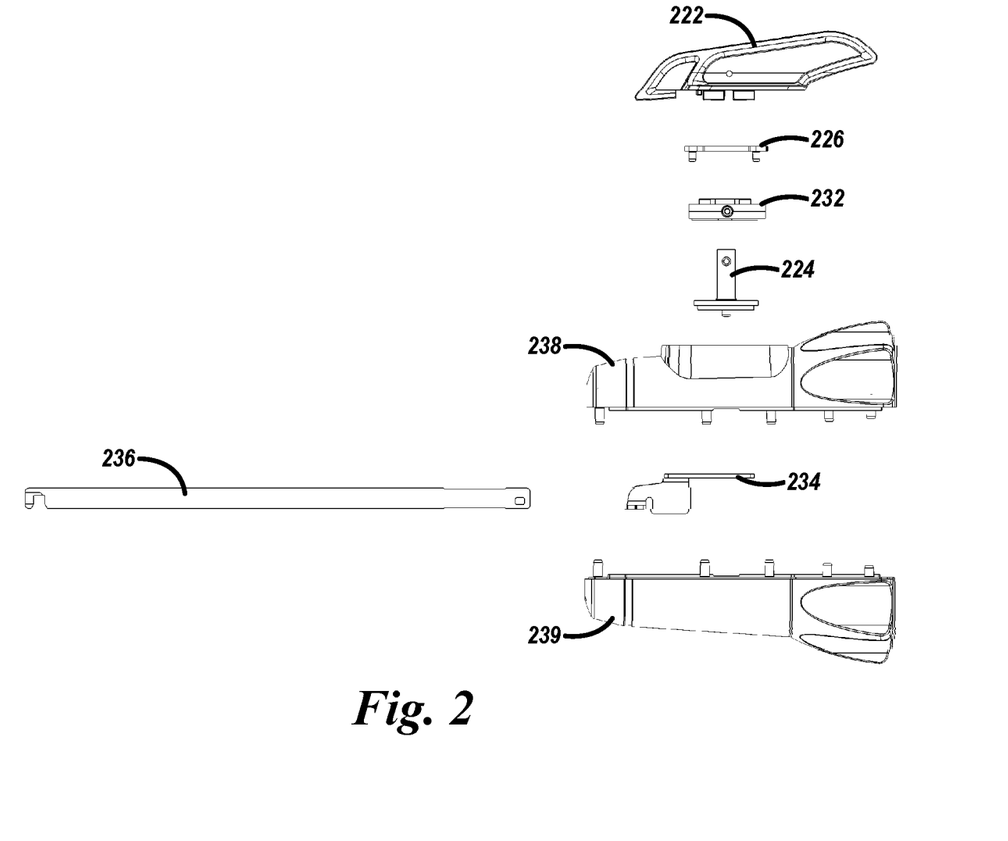
FIG. 2 is a schematic diagram of an articulation assembly in accordance with a number of embodiments of the present disclosure.

FIG. 2 is a schematic diagram of an articulation assembly in accordance with a number of embodiments of the present disclosure. In some examples, the articulation assembly can include a knob 222, a cam 224, a cover 226, a housing 232, a number of springs 230-1, 230-2, a number of spheres 228-1, 228-2, a tab 234, an articulation arm 236, a radial position component 238, and a bottom 239.

The knob 222 can be coupled to the cam 224 via a pin, for example. The cam 224 can actuate rotationally in response to the knob 222 being rotationally actuated by a user. The cam 224 can be coupled to the housing 232 via the cover 226 fastened to the housing 232. The housing 232 can actuate rotationally in response to the cam 224 and the knob 222 being actuated rotationally by the user.

The housing 232 can include one or more openings. One or more springs 230-1, 230-2 and one or more spheres 228-1, 228-2 can be in the one or more openings of the housing 232. The one or more springs 230-1, 230-2 can be configured to bias the one or more spheres 228-1, 228-2 radially outward. The one or more spheres 228-1, 228-2 can be biased outward to and received by one or more slots of the radial position component 238. Each of the one or more slots of the radial position component 238 can be a knob position. The housing 232 can be coupled to the radial position component 238 via the cover 226 and/or cam 224.

In some examples, the one or more spheres 228-1, 228-2 can move radially inward between positions of the radial position component 238 as the knob 222 is being actuated rotationally. The one or more spheres 228-1, 228-2 biased outward to a slot and/or knob position can maintain the articulation assembly in that position until the knob 222 is actuated rotationally by a user.

In a number of embodiments, the cam 224 is coupled to a tab 234. The cam 224 can include a pin member to move linearly in a slot in the tab 234. The tab 234 can be configured to move in a linear direction in response to the cam 224 actuating rotationally. In some examples, the tab 234 can be coupled to an articulation arm 236.

The articulation arm 236 can move in a linear direction in response to the tab 234 moving in the linear direction. In some examples, the articulation arm 236 and the tab 234 can move in a linear distal direction in response to the housing 232, cam 224, and knob 222 rotating counterclockwise. The articulation arm 236 and the tab 234 can move in a linear proximal direction in response to the housing 232, cam 224, and knob 222 rotating clockwise.

The articulation arm 236 can be coupled to the reloadable cartridge assembly (e.g., reloadable cartridge assembly 103 in FIG. 1). The reloadable cartridge assembly can rotate counterclockwise in response to the articulation arm 236 moving in the linear distal direction as a result of the user rotating the knob 222 in a counterclockwise direction. The reloadable cartridge assembly can rotate clockwise in response to the articulation arm 236 moving in the linear proximal direction as a result of the user rotating the knob 222 in a clockwise direction.

Figure 3A:
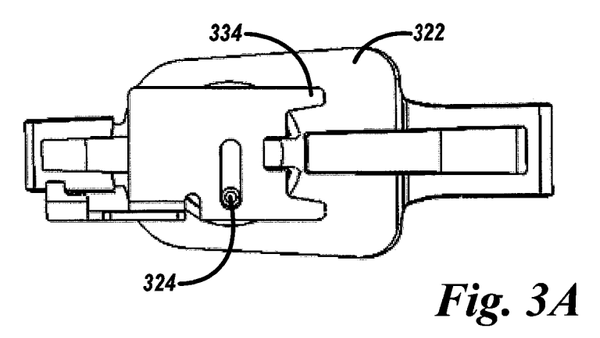
FIG. 3A is a schematic diagram of an articulation assembly including a knob, a cam, and a tab in a 0 degree knob position in accordance with a number of embodiments of the present disclosure.

FIG. 3A is a schematic diagram of an articulation assembly including a knob 322, a cam 324, and a tab 334 in a 0 degree knob position in accordance with a number of embodiments of the present disclosure.

As discussed above, the cam 324 can include a pin member. The pin member can be a part of the cam 324 or coupled to the cam 324. The location of the pin member on the cam 324 can determine whether the reloadable cartridge assembly (e.g., reloadable cartridge assembly 103 in FIG. 1) rotates counterclockwise or clockwise in response to the user rotating the knob 322 counterclockwise or clockwise.

For example, with the location of the pin member of the cam 324 shown in FIG. 3A, the tab 334 can move in a linear distal direction causing the reloadable cartridge assembly (e.g., reloadable cartridge assembly 103 in FIG. 1) to move counterclockwise in response to the knob 322 rotating counterclockwise and the tab 324 can move in a linear proximal direction causing the reloadable cartridge assembly to move clockwise in response to the knob 322 rotating clockwise.

In some examples, the pin member of the cam 324 can be located in a location on the cam 324, such that the reloadable cartridge assembly (e.g., reloadable cartridge assembly 103 in FIG. 1) will rotate clockwise in response to the knob 322 rotating counterclockwise and the reloadable cartridge assembly will rotate counterclockwise in response to the knob 322 rotating clockwise.

Figure 3B:
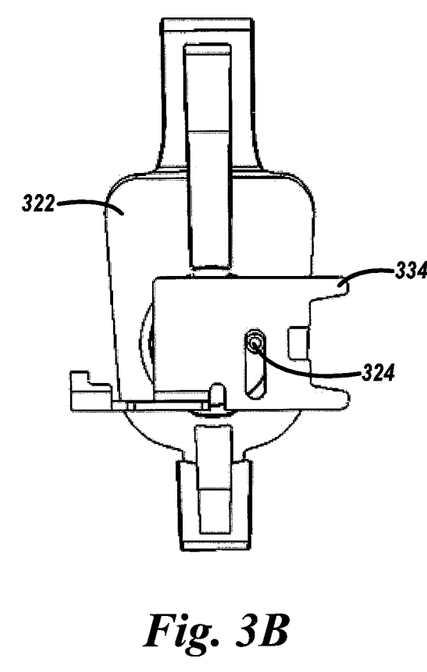
FIG. 3B is a schematic diagram of an articulation assembly including a knob, a cam, and a tab in a 90 degree knob position in accordance with a number of embodiments of the present disclosure.

FIG. 3B is a schematic diagram of an articulation assembly including a knob 322, a cam 324, and a tab 334 in a 90 degree knob position in accordance with a number of embodiments of the present disclosure.

With the location of the pin member of the cam 324 shown in FIG. 3B, the reloadable cartridge assembly (e.g., reloadable cartridge assembly 103 in FIG. 1) can be in a 45 degree operation mode in response to the knob 322 being in the 90 degree knob position.

In some examples, the pin member of the cam 324 can be located in a location on the cam 324, such that the reloadable cartridge assembly (e.g., reloadable cartridge assembly 103 in FIG. 1) will be in a −45 degree operation mode in response to the knob 322 being in a 90 degree knob position.

Figure 3C:
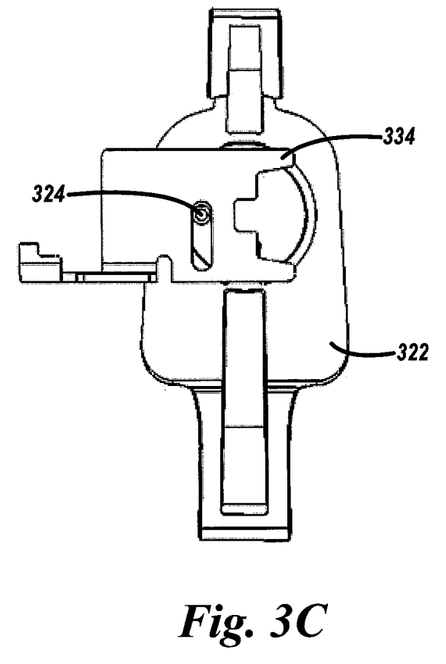
FIG. 3C is a schematic diagram of an articulation assembly including a knob, a cam, and a tab in a −90 degree knob position in accordance with a number of embodiments of the present disclosure.

FIG. 3C is a schematic diagram of an articulation assembly including a knob 322, a cam 324, and a tab 334 in a −90 degree knob position in accordance with a number of embodiments of the present disclosure.

With the location of the pin member of the cam 324 shown in FIG. 3C, the reloadable cartridge assembly (e.g., reloadable cartridge assembly 103 in FIG. 1) can be in a −45 degree operation mode in response to the knob 322 being in the −90 degree knob position.

In some examples, the pin member of the cam 324 can be located in a location on the cam 324, such that the reloadable cartridge assembly (e.g., reloadable cartridge assembly 103 in FIG. 1) will be in a 45 degree operation mode in response to the knob 322 being in a −90 degree knob position.

Figure 4A:
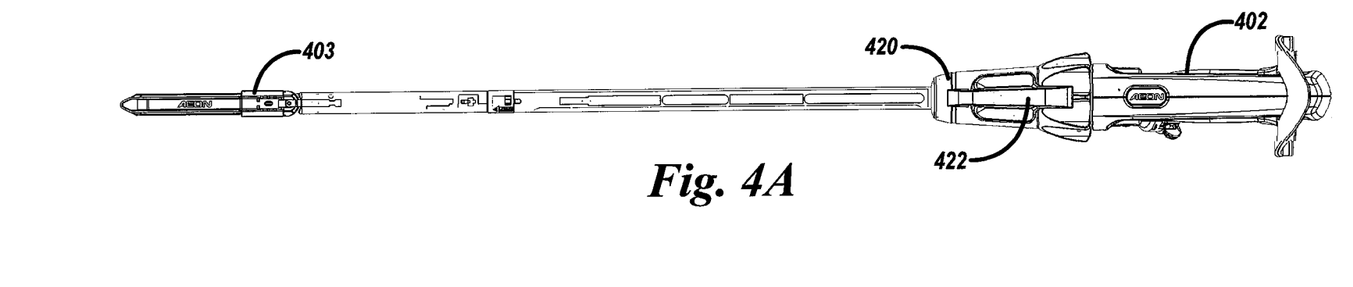
FIG. 4A is a schematic diagram of an apparatus including a surgical handle assembly apparatus including an articulation assembly and a reloadable cartridge assembly in a 0 degree operation position and an articulation assembly in accordance with a number of embodiments of the present disclosure.

FIG. 4A is a schematic diagram of an apparatus including a surgical handle assembly apparatus 402 including an articulation assembly 420 and a reloadable cartridge assembly 403 in a 0 degree operation position in accordance with a number of embodiments of the present disclosure. The articulation assembly 420 can include a knob 422.

In a number of embodiments, the articulation assembly 420 can be configured to maintain the reloadable cartridge assembly 403 in an operation position corresponding to a knob position. In this example, the knob 422 is maintained in a 0 degree knob position. As such, the reloadable cartridge assembly 403 is in the corresponding 0 degree operation position and is maintained in the 0 degree operation position as long as the knob 422 is maintained in the 0 degree knob position.

The articulation assembly 420 can be configured to actuate the reloadable cartridge assembly 403 from a first operation position, for example a 0 degree operation position, corresponding to a first knob position, for example a 0 degree knob position, to a different operation position corresponding to a different knob position.

The reloadable cartridge assembly 403 can be actuated to a number of operation positions totaling approximately 90 degrees. For example, the reloadable cartridge assembly 403 can be actuated to a number of operation positions between approximately 45 degrees and −45 degrees in response to the knob 422 being actuated to a number of knob positions between approximately 90 degrees and −90 degrees. The number of operation positions can depend on the number of corresponding knob positions and/or slots in the radial position component (e.g., radial position component 238 in FIG. 2).

Figure 4B:
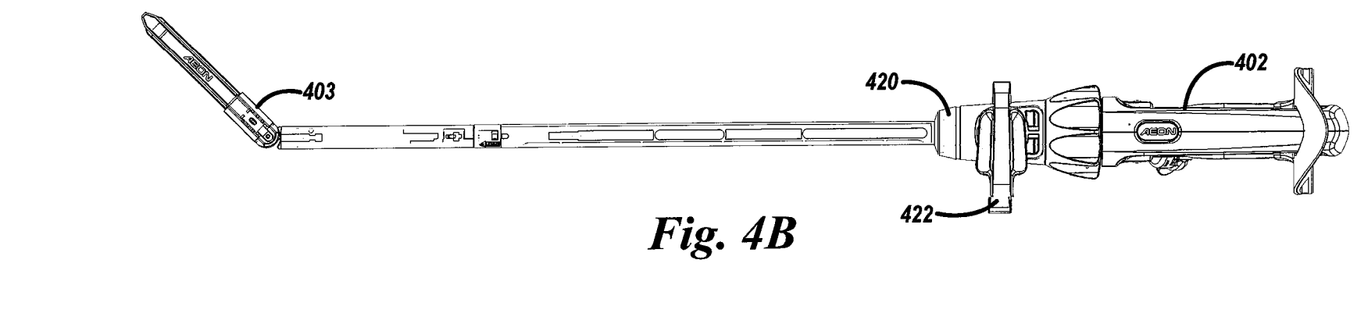
FIG. 4B is a schematic diagram of an apparatus including a surgical handle assembly apparatus including an articulation assembly and a reloadable cartridge assembly in a 45 degree operation position and an articulation assembly in accordance with a number of embodiments of the present disclosure.

FIG. 4B is a schematic diagram of an assembly apparatus including a surgical handle assembly apparatus 402 including an articulation assembly 420 and a reloadable cartridge assembly 403 in a 45 degree operation position in accordance with a number of embodiments of the present disclosure. In some examples the articulation assembly 420 can include a knob 422.

In a number of embodiments, the articulation assembly 420 can be configured to maintain the reloadable cartridge assembly 403 in an operation position corresponding to a knob position. In this example, the knob 422 is maintained in a 90 degree knob position. As such, the reloadable cartridge assembly 403 is in the corresponding 45 degree operation position and is maintained in the 45 degree operation position as long as the knob 422 is maintained in the 90 degree knob position.

In some examples, the reloadable cartridge assembly 403 can be actuated to a number of operation positions from the 45 degree operation position in response to the knob 422 being actuated by a user.

The articulation assembly 420 can be configured to actuate the reloadable cartridge assembly 403 from the 45 degree operation position corresponding to a 90 degree knob position, to a different operation position corresponding to a different knob position.

Figure 4C:
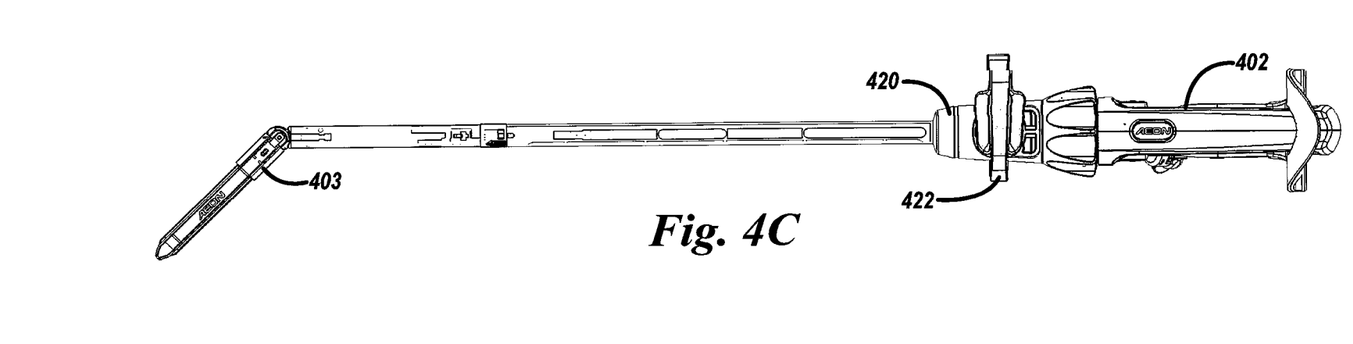
FIG. 4C is a schematic diagram of an apparatus including a surgical handle assembly apparatus including an articulation assembly and a reloadable cartridge assembly in a −45 degree operation position and an articulation assembly in accordance with a number of embodiments of the present disclosure.

FIG. 4C is a schematic diagram of an assembly apparatus including a surgical handle assembly apparatus 402 including an articulation assembly 420 and a reloadable cartridge assembly 403 in a −45 degree operation position in accordance with a number of embodiments of the present disclosure. In some examples the articulation assembly 420 can include a knob 422.

In a number of embodiments, the articulation assembly 420 can be configured to maintain the reloadable cartridge assembly 403 in an operation position corresponding to a knob position. In this example, the knob 422 is maintained in a −90 degree knob position. As such, the reloadable cartridge assembly 403 is in the corresponding −45 degree operation position and is maintained in the −45 degree operation position as long as the knob 422 is maintained in the −90 degree knob position.

In some examples, the reloadable cartridge assembly 403 can be actuated to a number of operation positions from the −45 degree operation position in response to the knob 422 being actuated by a user.

The articulation assembly 420 can be configured to actuate the reloadable cartridge assembly 403 from the −45 degree operation position corresponding to the −90 degree knob position to a different operation position corresponding to a different knob position.

Figure 5A:
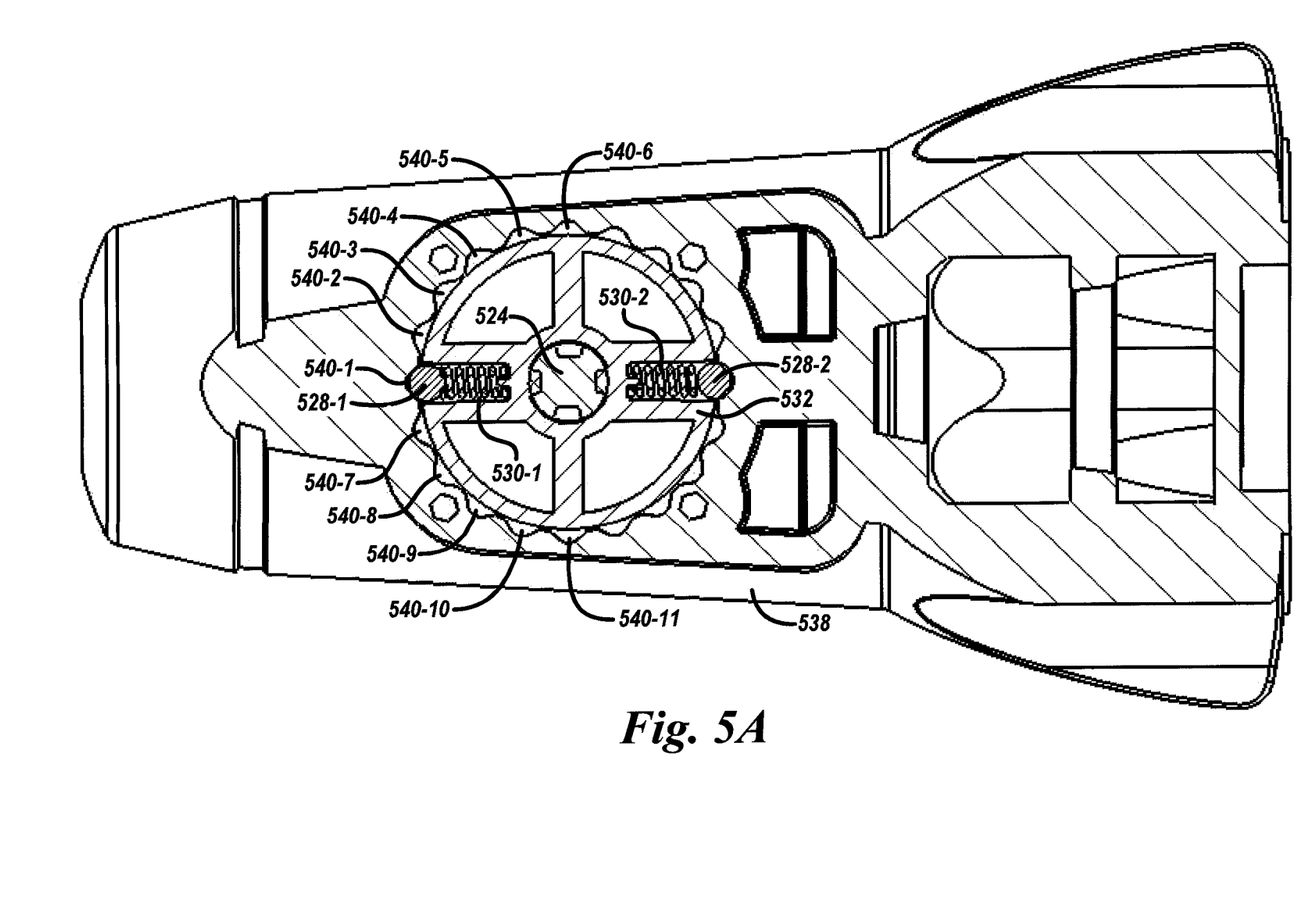
FIG. 5A is a schematic diagram of an articulation assembly including a housing, one or more spheres, one or more springs, a radial position component, and a cam in a 0 degree knob position in accordance with a number of embodiments of the present disclosure.

FIG. 5A is a schematic diagram of an articulation assembly including a housing 532, one or more spheres 528-1, 528-2, one or more springs 530-1, 530-2, a radial position component 538, and a cam 524 in a 0 degree knob position in accordance with a number of embodiments of the present disclosure. The radial position component 538 can include a number of slots 540-1, 540-2, . . . , 540-11.

In a number of embodiments, the cam 524 can actuate rotationally in response to the knob (e.g., knob 422 in FIG. 4) being rotationally actuated by a user. The cam 524 can be coupled to the housing 532. The housing 532 can actuate rotationally in response to the cam 524 and the knob being actuated rotationally.

The housing 532 can include one or more openings. One or more springs 530-1, 530-2 and one or more spheres 528-1, 528-2 can be in the one or more openings of the housing 532. The one or more springs 530-1, 530-2 can be configured to bias the one or more spheres 528-1, 528-2 radially outward. The one or more spheres 528-1, 528-2 can be biased outward to and received by one or more slots 540-1, 540-2, . . . , 540-10 of the radial position component 538. Each of the one or more slots 540-1, 540-2, . . . , 540-11 of the radial position component 538 can be a knob position.

In some examples, the one or more spheres 528-1, 528-2 can move radially inward between slots 540-1, 540-2, . . . , 540-11 of the radial position component 538 as the knob (e.g., knob 422 in FIG. 2) is being actuated rotationally. The one or more spheres 528-1, 528-2 biased outward to the one or more slots 540-1, 540-2, . . . , 540-11 can maintain the articulation assembly (e.g., articulation assembly 420 in FIG. 2) in a knob position until the knob is actuated rotationally by a user.

In a number of embodiments, a force needed to actuate the knob (e.g., knob 422 in FIG. 2) from a first knob position 540-1 to a third knob position 540-3 is different than the force needed to actuate the knob from the third knob position 540-3 to a sixth knob position 540-6. For example, the force to move the knob from a first knob position 540-1 to a sixth knob position 540-6 can increase as the knob moves through the number of knob positions between the first knob position 540-1 and the sixth knob position 540-6. When the knob is in the sixth knob position 540-6, the housing 532 is biased to return to the first knob position 540-1, but the one or more springs 530-1, 530-2 have sufficient force to hold the one or more spheres 528-1, 5428-2 in the one or more slots 540-1, 540-2, . . . , 540-11 of the radial position component 538 to maintain the knob in the sixth position 540-6.

Figure 5B:
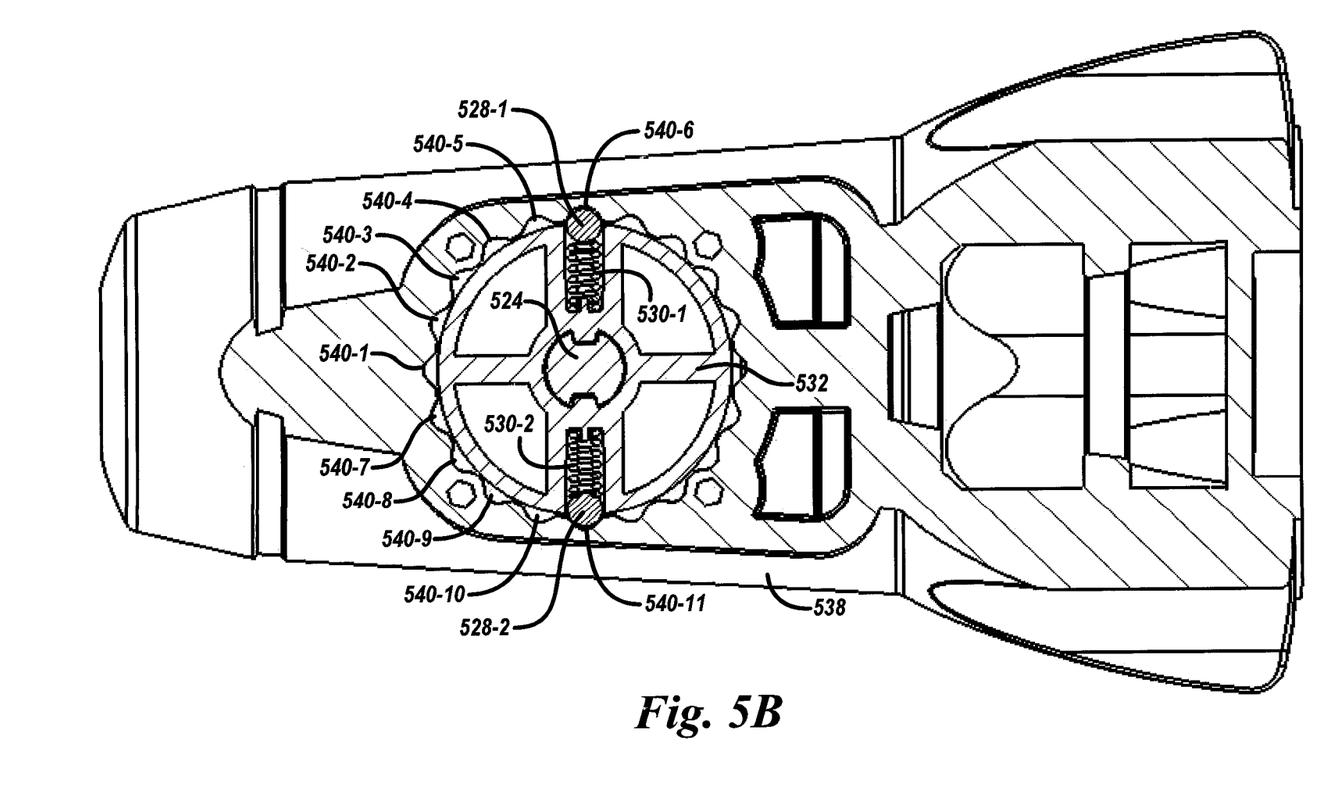
FIG. 5B is a schematic diagram of an articulation assembly including a housing, one or more spheres, one or more springs, a radial position component, and a cam in a 90 degree knob position in accordance with a number of embodiments of the present disclosure.

FIG. 5B is a schematic diagram of an articulation assembly including a housing 532, one or more spheres 528-1, 528-2, one or more springs 530-1, 530-2, a radial position component 538, and a cam 524 in a 90 degree knob position in accordance with a number of embodiments of the present disclosure. The radial position component 538 can include a number of slots 540-1, 540-2, . . . , 540-11.

In a number of embodiments, the articulation assembly (e.g., articulation assembly 420 in FIG. 2) can be in a 90 degree knob position when a first sphere 528-1 is located in a sixth slot 540-6 of the radial position component 538. In some examples, a second sphere 528-2 can be located in an eleventh slot 540-11 of the radial position component 538.

A user can rotate the knob (e.g., knob 422 in FIG. 4) approximately 90 degrees from the 0 degree knob position at slot 540-1 of the radial position component 538 past a number of knob positions 540-2, 540-3, . . . , 540-5 to get to the sixth knob position 540-6. The sixth knob position 540-6 can correspond to a 45 degree operation mode of the reloadable cartridge assembly (e.g., reloadable cartridge assembly 403 in FIG. 4). The number of slots between the first slot 540-1 and the sixth slot 540-6, specifically slots 540-2, 540-3, 540-4, and 540-5, can correspond to knob positions between 0 and 90 degrees and operation positions of the reloadable cartridge assembly between 0 and 45 degrees, for example.

In some examples, the number of slots between the first slot 540-1 and the sixth slot 540-6 can correspond to knob positions between 0 and 180 degrees or less and an operation position of the reloadable cartridge assembly between 0 and 90 degrees or less, for example.

Figure 5C:
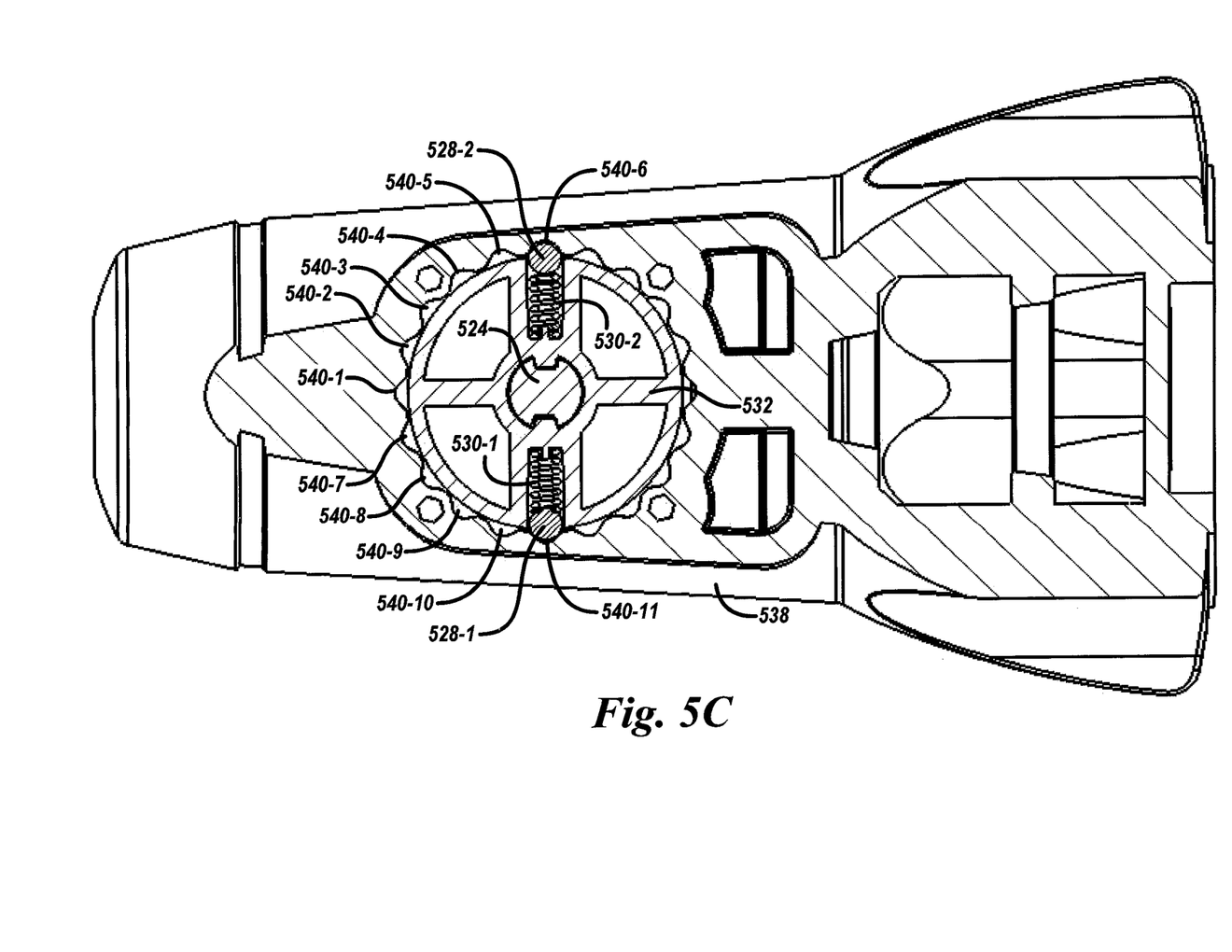
FIG. 5C is a schematic diagram of an articulation assembly including a housing, one or more spheres, one or more springs, a radial position component, and a cam in a −90 degree knob position in accordance with a number of embodiments of the present disclosure.

FIG. 5C is a schematic diagram of an articulation assembly including a housing 532, one or more spheres 528-1, 528-2, one or more springs 530-1, 530-2, a radial position component 538, and a cam 524 in a −90 degree knob position in accordance with a number of embodiments of the present disclosure. The radial position component 538 can include a number of slots 540-1, 540-2, . . . , 540-11.

In a number of embodiments, the articulation assembly (e.g., articulation assembly 420 in FIG. 2) can be in a −90 degree knob position when a first sphere 528-1 is located in an eleventh slot 540-11 of the radial position component 538. In some examples, a second sphere 528-2 can be located in a sixth slot 540-6 of the radial position component 538.

A user can rotate the knob (e.g., knob 422 in FIG. 4) approximately −90 degrees from the 0 degree knob position at slot 540-1 of the radial position component 538 past a number of knob positions 540-7, 540-8, . . . , 540-10 to get to the eleventh knob position 540-11. The eleventh knob position 540-11 can correspond to a −45 degree operation mode of the reloadable cartridge assembly (e.g., reloadable cartridge assembly 403 in FIG. 4). The number of slots between the first slot 540-1 and the eleventh slot 540-11, specifically slots 540-7, 540-8, 540-9, and 540-10, can correspond to knob positions between 0 and −90 degrees and operation positions of the reloadable cartridge assembly between 0 and −45 degrees, for example.

In some examples, the number of slots between the first slot 540-1 and the eleventh slot 540-11 can correspond to a knob position between 0 and −180 degrees or less and an operation position of the reloadable cartridge assembly between 0 and 90 degrees or less, for example.

Although specific embodiments have been illustrated and described herein, those of ordinary skill in the art will appreciate that an arrangement calculated to achieve the same results can be substituted for the specific embodiments shown. This disclosure is intended to cover adaptations or variations of one or more embodiments of the present disclosure. It is to be understood that the above description has been made in an illustrative fashion, and not a restrictive one. Combination of the above embodiments, and other embodiments not specifically described herein will be apparent to those of skill in the art upon reviewing the above description. The scope of the one or more embodiments of the present disclosure includes other applications in which the above structures and processes are used. Therefore, the scope of one or more embodiments of the present disclosure should be determined with reference to the appended claims, along with the full range of equivalents to which such claims are entitled.

In the foregoing Detailed Description, some features are grouped together in a single embodiment for the purpose of streamlining the disclosure. This method of disclosure is not to be interpreted as reflecting an intention that the disclosed embodiments of the present disclosure have to use more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. An apparatus, comprising:
   a reloadable cartridge assembly; and
   a surgical handle assembly including an articulation assembly configured to maintain the reloadable cartridge assembly in a first operation position, the articulation assembly comprising:
   a knob in a nonzero degree first knob position coupled to a housing, wherein the knob is biased to return to a zero degree second knob position, wherein a force needed to actuate the knob from the nonzero degree first knob position to a nonzero degree third knob position is less than a force needed to actuate the knob from the nonzero degree third knob position to a nonzero degree fourth knob position, wherein the third knob position is located at a greater degree than the first knob position and the fourth knob position is located at a greater degree than the third knob position; and
   a spring coupled to the housing configured to bias a sphere radially outward to a first slot of a radial position component to maintain the knob in the nonzero degree first knob position, a second slot of the radial position component to maintain the knob in the zero degree second knob position, a third slot of the radial position component to maintain the knob in the nonzero degree third knob position, and a fourth slot of the radial position component to maintain the knob in the nonzero degree fourth knob position.

2. The apparatus of claim 1, wherein the articulation assembly is configured to maintain the reloadable cartridge assembly in one of a plurality of operation positions including the first operation position.

3. The apparatus of claim 1, wherein the articulation assembly further includes a cam coupled to the knob.

4. The apparatus of claim 3, wherein the cam is coupled to the housing via a cover.

5. The apparatus of claim 4, wherein the articulation assembly further includes a tab coupled to the housing.

6. The apparatus of claim 1, wherein the radial position component includes a plurality of slots.

7. An apparatus, comprising:
   a reloadable cartridge assembly; and
   a surgical handle assembly including an articulation assembly configured to actuate the reloadable cartridge assembly from a first operation position to a second operation position, the articulation assembly comprising:
   a knob coupled to a housing configured to actuate rotationally from a first knob position to a second knob position, wherein a force needed to actuate the knob from the first knob position to the second knob position is less than a force needed to actuate the knob from the second knob position to a third knob position and the force needed to actuate the knob from the second knob position to the third knob position is less than a force needed to actuate the knob from the third knob position to a fourth knob position, and wherein the first knob position is in a zero degree knob position, the second knob position is in a nonzero degree knob position, and a degree knob position of the third knob position is greater than the nonzero degree knob position of the second knob position and a degree knob position of the fourth knob position is greater than the degree knob position of the third knob position; and
   a spring coupled to the housing configured to bias a sphere radially outward from a first slot of a radial position component to a second slot of the radial position component in response to actuating the knob from the first knob position to the second knob position, from the second slot of the radial position component to a third slot of the radial position component in response to actuating the knob from the second knob position to the third knob position, from the third slot of the radial position component to a fourth slot of the radial position component in response to actuating the knob from the third knob position to the fourth knob position.

8. The apparatus of claim 7, wherein the sphere moves radially inward between the first slot and the second slot of the radial position component.

9. The apparatus of claim 7, wherein the reloadable cartridge assembly is configured to rotate about an axis of a particular plane from the first operation position to the second operation position.

10. The apparatus of claim 7, wherein the articulation assembly is configured to maintain the reloadable cartridge assembly in the second operation position.

11. The apparatus of claim 7, wherein the knob is actuated to the third knob position and the reloadable cartridge assembly is actuated to a third operation position.

12. The apparatus of claim 7, wherein the knob is actuated clockwise from the first knob position to the second knob position to actuate the reloadable cartridge assembly clockwise from the first operation position to the second operation position.

13. An apparatus, comprising:
   a reloadable cartridge assembly configured to rotate about an axis of a particular plane to a plurality of operation positions;
   a surgical handle assembly including an articulation assembly configured to actuate the reloadable cartridge assembly to one of the plurality of operation positions and maintain the reloadable cartridge assembly in one of the plurality of operation positions, the articulation assembly comprising:
   a knob coupled to a housing configured to actuate rotationally from a first knob position to a second knob position, wherein a force needed to actuate the knob from the first knob position to the second knob position is less than a force needed to actuate the knob from the second knob position to a third knob position and the force needed to actuate the knob from the second knob position to the third knob position is less than a force needed to actuate the knob from the third knob position to a fourth knob position, and wherein the first knob position is in a zero degree knob position, the second knob position is in a nonzero degree knob position, and a degree knob position of the third knob position is greater than the nonzero degree knob position of the second knob position and a degree knob position of the fourth knob position is greater than the degree knob position of the third knob position; and a spring coupled to the housing configured to bias a sphere radially outward from a first slot of a radial position component corresponding to the first knob position to a second slot of the radial position component corresponding to the second knob position, from the second slot of the radial position component to a third slot of the radial position component corresponding to the third knob position, from the third slot of the radial position component to a fourth slot of the radial position component corresponding to the fourth knob position.

14. The apparatus of claim 13, wherein a first operation position of the reloadable cartridge assembly is 90 degrees from a second operation position of the reloadable cartridge assembly.

15. The apparatus of claim 13, wherein the first knob position is 180 degrees from the fourth knob position.

16. The apparatus of claim 13, wherein the articulation assembly further includes a cam coupled to the knob, a tab coupled to the cam, and an articulation arm coupled to the tab.

17. The apparatus of claim 16, wherein the articulation arm and the tab move in a linear distal direction in response to the cam rotating counterclockwise.

18. The apparatus of claim 17, wherein the reloadable cartridge assembly rotates counterclockwise in response to the articulation arm and the tab moving in the linear distal direction.

19. The apparatus of claim 16, wherein the articulation arm and the tab move in a linear proximal direction in response to the cam rotating clockwise.

20. The apparatus of claim 19, wherein the reloadable cartridge assembly rotates clockwise in response to the articulation arm and the tab moving in the linear proximal direction.

* * * * *